United States Patent
Jung et al.

(10) Patent No.: US 7,655,807 B2
(45) Date of Patent: Feb. 2, 2010

(54) LOW MOLECULAR WEIGHT CONJUGATED NITROGEN COMPOUNDS AND DEVICES FABRICATED USING THE SAME

(75) Inventors: Won Cheol Jung, Seoul (KR); Jean Roncali, Angers (FR); Sang Cheol Park, Seoul (KR); Antonio Cravino, Angers (FR); Philippe Leriche, Angers (FR); Pierre Frere, Angers (FR); Sophie Roquet, Angers (FR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 12/034,312

(22) Filed: Feb. 20, 2008

(65) Prior Publication Data

US 2008/0214839 A1    Sep. 4, 2008

Related U.S. Application Data

(62) Division of application No. 11/348,243, filed on Feb. 7, 2006, now Pat. No. 7,358,375.

(30) Foreign Application Priority Data

Aug. 8, 2005   (KR) ............................... 2005-72224

(51) Int. Cl.
C07D 333/16   (2006.01)
(52) U.S. Cl. ....................................................... 549/65
(58) Field of Classification Search .................... 549/65
See application file for complete search history.

(56) References Cited

OTHER PUBLICATIONS

Yamamoto et al., Macromolecules (2002), vol. 35(15), pp. 5782-5788.*
Abstract of Yamamoto et al., cited above.*
Kotani, S. et al., *Journal of Organometallic Chemistry*, 429 (1992) 403-413, Elsevier Sequoia S.A., Lausanne, JOM 22172.
March J. *Advanced Organic Chemistry*, Wiley 1992, Fourth edition, p. 82.
Seeboth et al., Z. Chem, 16. Jg. (1976) Heft 10, pp. 399-400.

* cited by examiner

*Primary Examiner*—Taofiq A Solola
(74) *Attorney, Agent, or Firm*—Cantor Colburn LLP

(57) ABSTRACT

Low molecular weight conjugated nitrogen compounds having linear conjugated chains, and devices fabricated using the conjugated nitrogen compounds as organic semiconductor materials, hole conducting materials, or light-emitting materials. The conjugated nitrogen compounds can be spin-coated at room temperature, are stable, and has superior electrical conductivity.

12 Claims, 3 Drawing Sheets

LOW MOLECULAR WEIGHT CONJUGATED NITROGEN COMPOUNDS AND DEVICES FABRICATED USING THE SAME

CROSS-REFERENCE TO RELATED PATENT APPLICATION

This application is a divisional of U.S. application Ser. No. 11/348,243 filed Feb. 7, 2006, now U.S. Pat. No. 7,358,375 which is a non-provisional application claiming priority under 35 U.S.C. §119(a) to Korean Patent Application No. 2005-72224 filed on Aug. 8, 2005, both of which are herein incorporated by reference.

BACKGROUND

1. Field of the Disclosure

Embodiments of the present disclosure relate to low molecular weight conjugated nitrogen compounds and devices fabricated using the conjugated nitrogen compounds. More particularly, embodiments of the present disclosure relate to low molecular weight conjugated nitrogen compounds having linear conjugated chains, and devices fabricated using the conjugated nitrogen compounds as organic semiconductor materials, hole conducting materials, or light-emitting materials.

2. Description of the Related Art

Recent research has been concentrated on low molecular weight organic materials, such as pentacene, as organic semiconductor materials, and some research groups have paid attention to high molecular weight organic materials.

Although low molecular weight organic materials, e.g., pentacene, have been reported to have a high charge carrier mobility and a high on/off current ratio ($I_{on}/I_{off}$ ratio), they necessitate the use of expensive vacuum deposition apparatuses for fabricating devices and have a difficulty in forming fine patterns. Accordingly, low molecular weight organic materials are not attractive for the manufacture of large-area displays at low costs.

Unlike low molecular weight organic materials, polythiophene-based high molecular weight organic materials are easily formed into solutions, and can be formed into thin films by screen printing, ink-jet and roll printing techniques. For these reasons, it is reported that the high molecular weight organic materials have advantages in the manufacture of large-area displays at low costs.

However, since the high molecular weight organic materials have different oxidation potentials depending on their molecular weight distribution, which is a cause of instability, their application to the fabrication of devices presents considerable difficulties. In contrast, since the low molecular weight organic materials have a constant oxidation potential, they have been found to be advantageous in terms of stability.

Additionally, low molecular weight materials, e.g., tris-(8-hydroxyquinoline)aluminum (Alq), and high molecular weight materials, e.g., polyphenylenevinylene (PPV) and polyalkylthiophene (PAT), have been known as light-emitting materials. Like the above-mentioned organic semiconductor materials, low molecular weight light-emitting materials cannot be spin-coated at room temperature, while high molecular weight light-emitting materials can be coated by spin coating at room temperature. High molecular weight light-emitting materials still have the problem of instability.

SUMMARY

Therefore, embodiments of the present disclosure have been made in view of the above problems of the prior art, and it is an object of embodiments of the present disclosure to provide low molecular weight conjugated nitrogen compounds having linear conjugated chains as low molecular weight organic materials that can be spin-coated at room temperature and are stable when applied to the fabrication of devices, as well as have superior electrical conductivity.

In accordance with one aspect of embodiments of the present disclosure, there may be provided a low molecular weight conjugated nitrogen compound represented by Formula 1 below:

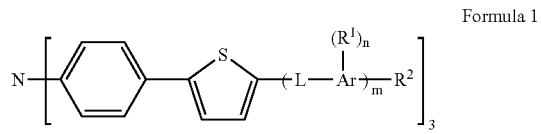

Formula 1 wherein L is a single bond or a vinylene group,

Ar is a $C_{3-30}$ aryl or heteroaryl group,

R1 and R2 are each independently selected from the group consisting of hydrogen; $C_{1-10}$ linear and branched alkyl groups; $C_{1-10}$ linear and branched alkoxy groups; $C_{1-10}$ linear and branched hydroxyalkyl groups; and $C_{1-10}$ linear and branched alkoxyalkyl groups, m is an integer between 1 and 5, and n is an integer between 1 and 3.

In accordance with another aspect of embodiments of the present disclosure, there may be provided a device fabricated using the low molecular weight conjugated nitrogen compound, as an organic semiconductor material, a hole conducting material or a light-emitting material. Preferably, the material can be spin-coated at room temperature, is stable when applied to the fabrication of the device, and has superior electrical conductivity.

BRIEF DESCRIPTION OF THE DRAWINGS

The above and other objects, features and other advantages of embodiments of the present disclosure will be more clearly understood from the following detailed description taken in conjunction with the accompanying drawings, in which.

DETAILED DESCRIPTION OF THE EMBODIMENTS

Figure 1:
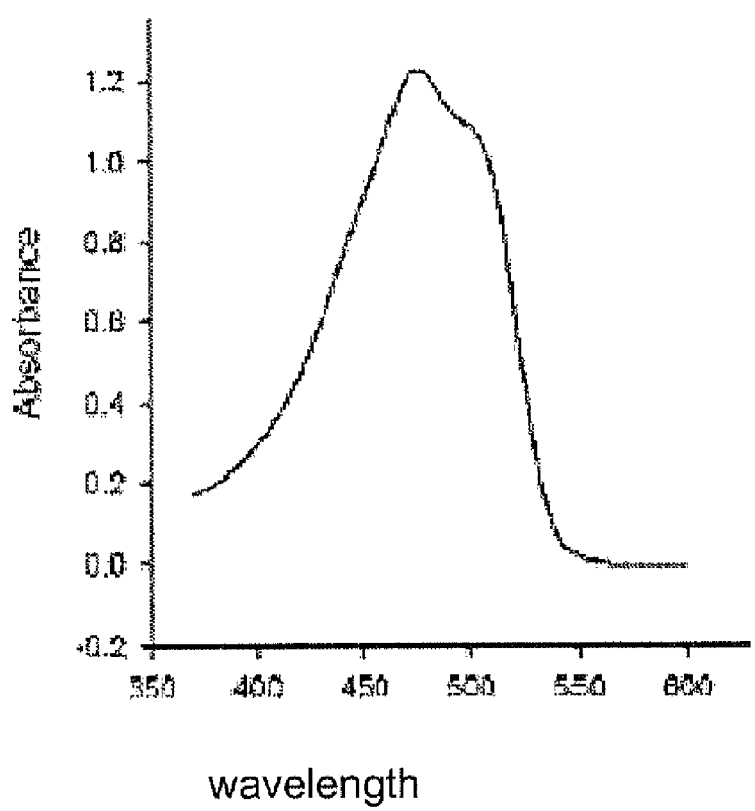
FIG. 1 is a UV-VIS absorption spectrum of a low molecular weight conjugated nitrogen compound synthesized in Preparative Example 1.

Embodiments of the present disclosure will now be described in more detail with reference to the accompanying drawings.

An embodiment of the present disclosure provides a low molecular weight conjugated nitrogen compound represented by Formula 1 below:

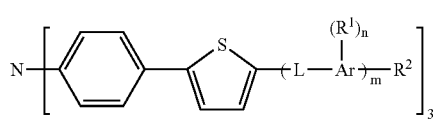

(1)

wherein L is a single bond or a vinylene group,

Ar is a $C_{3-30}$ aryl or heteroaryl group, $R^1$ and $R^2$ are each independently selected from the group consisting of hydrogen; $C_{1-10}$ linear and branched alkyl groups, $C_{1-10}$ linear and branched alkoxy groups, $C_{1-10}$ linear and branched hydroxyalkyl groups, and $C_{1-10}$ linear and branched alkoxyalkyl groups, m is an integer between 1 and 5, and n is an integer between 1 and 3.

The low molecular weight conjugated nitrogen compound of embodiments of the present disclosure may have a structure wherein three linear conjugated chains as side chains are bonded to one central nitrogen atom of the molecule. Since the conjugated nitrogen compound of embodiments of the present disclosure may have a low molecular weight, it may have a constant oxidation potential and thus may be stable. In addition, since the conjugated nitrogen compound of embodiments of the present disclosure is highly soluble in organic solvents, it can be coated by previously known coating techniques. Furthermore, since the conjugated nitrogen compound of embodiments of the present disclosure may have low oxidation levels, it may have superior electrical conductivity at low voltages.

A representative example of Ar in the low molecular weight conjugated nitrogen compound of Formula 1 according to embodiments of the present disclosure may be selected from the arylene and heteroarylene compounds of Formula 2 below:

Formula 2

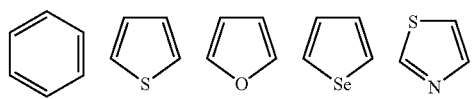

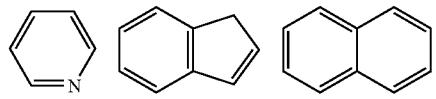

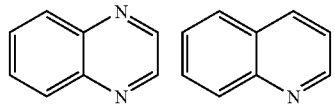

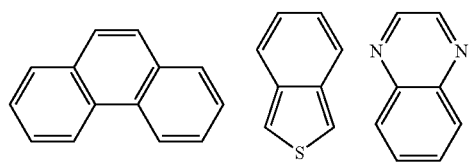

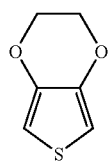

Thiophene, 3,4-ethylenedioxythiophene (EDOT), and phenyl are more preferred.

More specifically, the low molecular weight conjugated nitrogen compound of Formula 1 is preferably selected from the group consisting of compounds represented by Formulae 3 to 6 below:

Formula 3

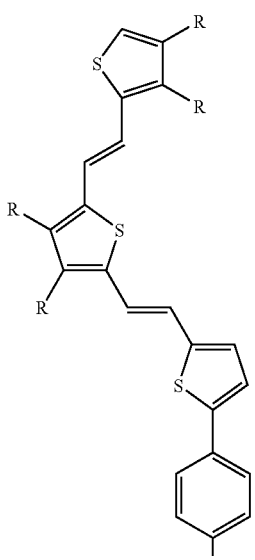

-continued
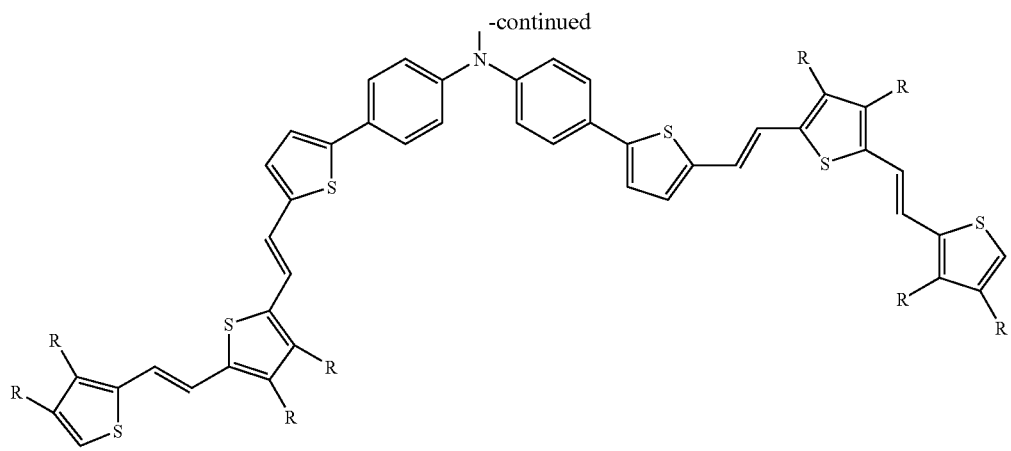
wherein R is selected from the group consisting of hydrogen; $C_{1-10}$ linear and branched alkyl groups; $C_{1-10}$ linear and branched alkoxy groups; $C_{1-10}$ linear and branched hydroxyalkyl groups; and $C_{1-10}$ linear and branched alkoxyalkyl groups;
Formula 4
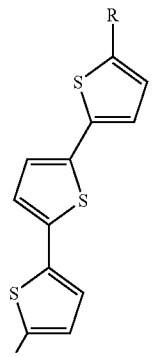
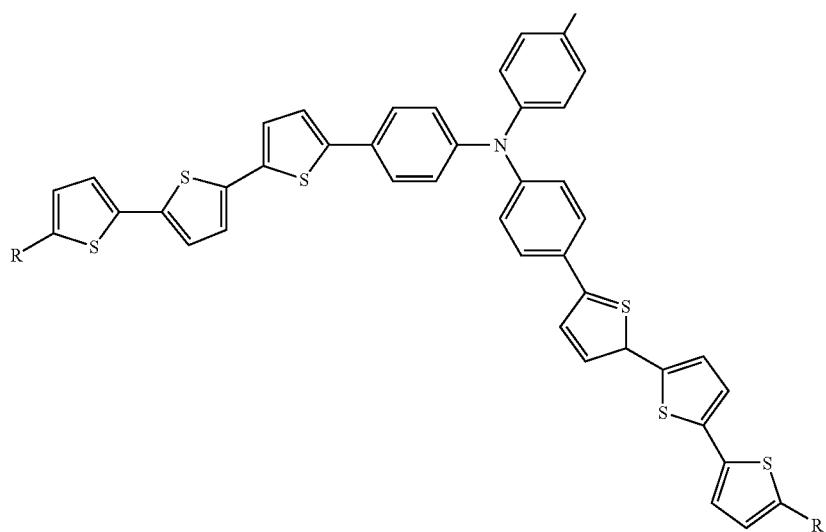

wherein R is as defined in Formula 3;
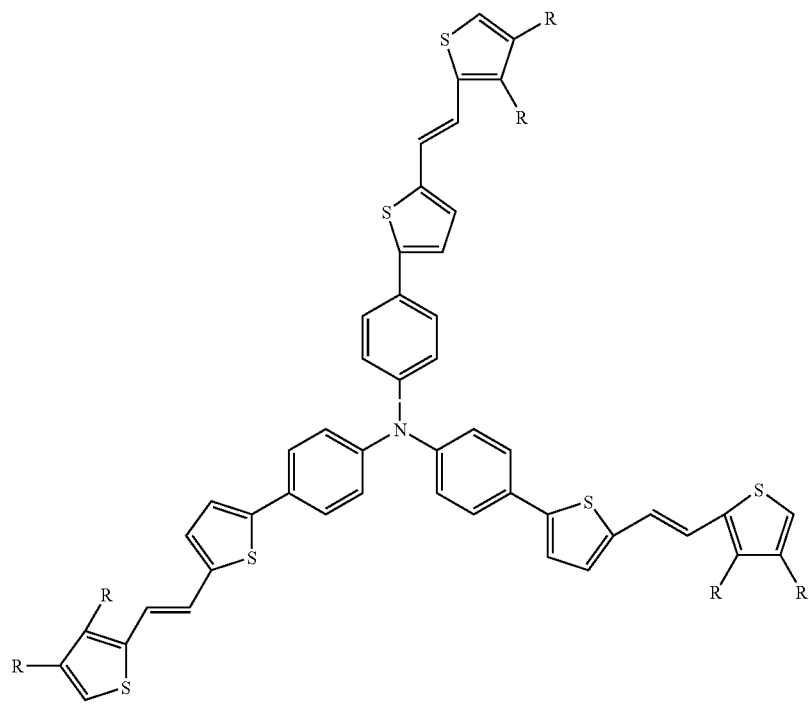
Formula 5
wherein R is as defined in Formula 3; and
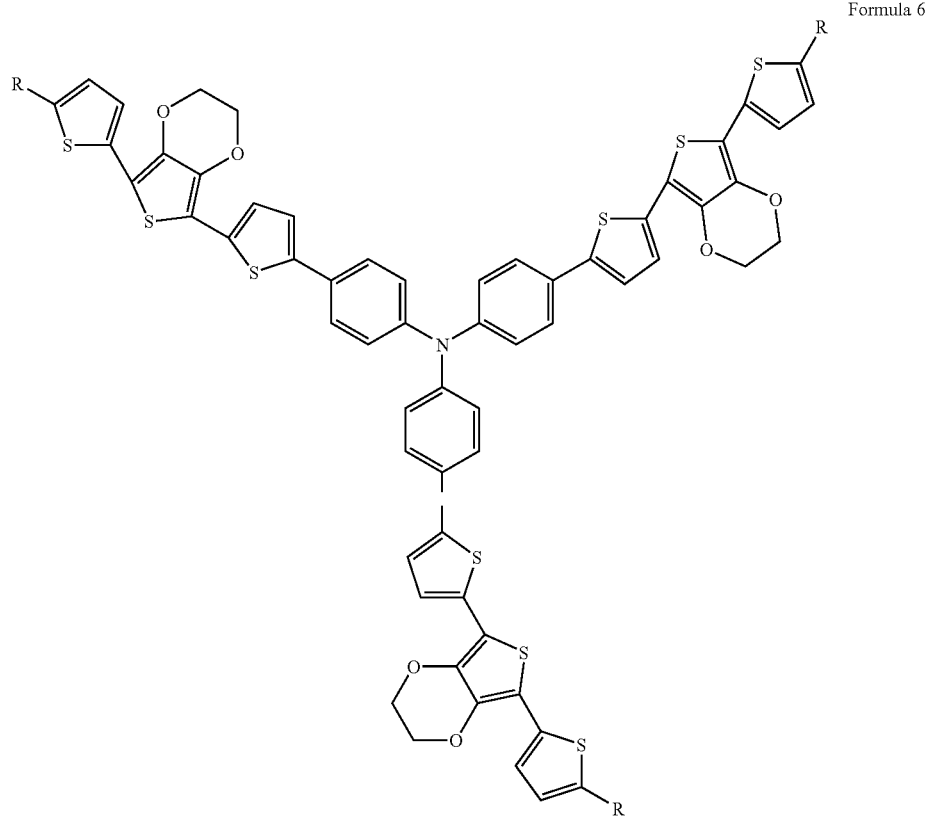
Formula 6 wherein R is as defined in Formula 3.

The low molecular weight conjugated nitrogen compound of embodiments of the present disclosure can be synthesized by chemical or electrochemical oxidation and condensation using an organometallic compound of a transition metal, such as nickel or palladium, which are representative polymerization processes of heteroaromatic compounds.

More preferably, there can be used a palladium (0) compound of Formula 7 below:

PdL$_4$   Formula 7 wherein L is a ligand selected from the group consisting of triphenylphosphine (PPh$_3$), triphenylarsine (AsPh$_3$), triphenylphosphite (P(OPh)$_3$), diphenylphosphinoferrocene (dppf, diphenylphosphino butane (dppb), acetate (OAc), and dibenzylideneacetone (dba).

Also, there may be used a palladium (II) compounds of Formulae 8 and 9 below:

PdL2X2   Formula 8 wherein L is as defined in Formula 7, and X is I, Br or Cl; and

PdL$_2$   Formula 9 wherein L is as defined in Formula 7.

Specifically, the compound of Formula 3 may be synthesized through the reaction routes shown in Reaction Scheme 1 below:

Reaction Scheme 1

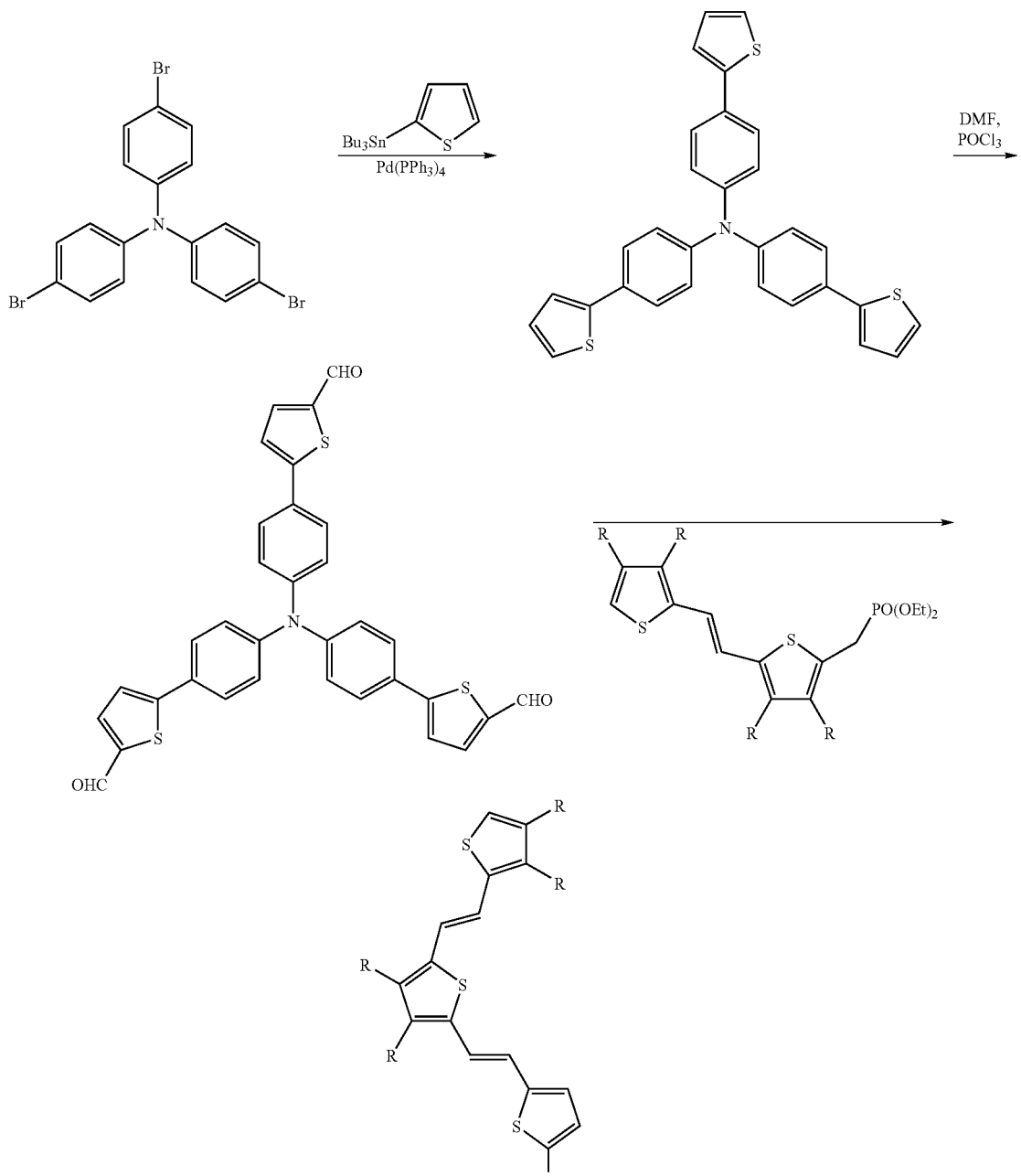

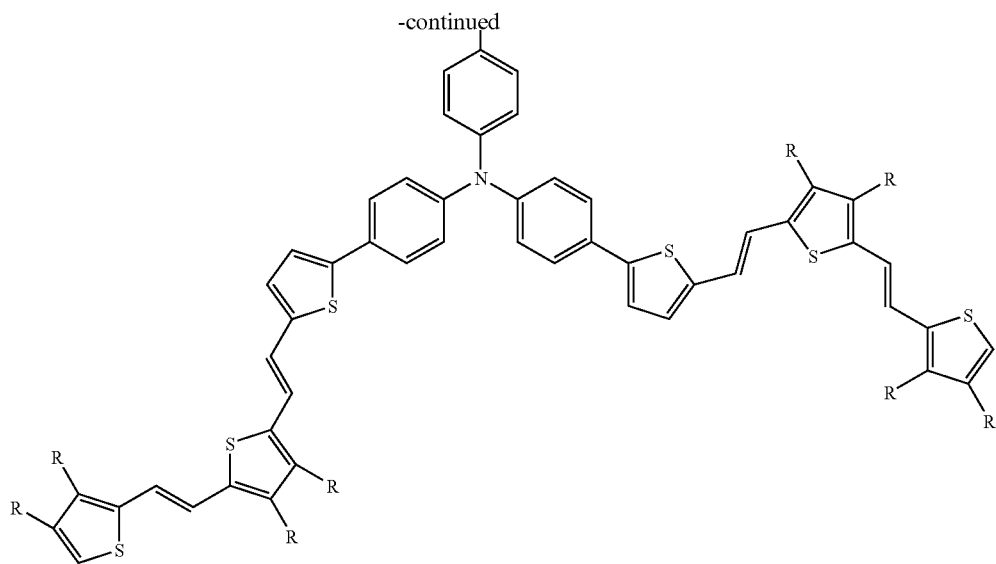
Further, the compounds of Formulae 4 to 6 may be synthesized through the respective reaction routes shown in Reaction Schemes 2 to 4 below:
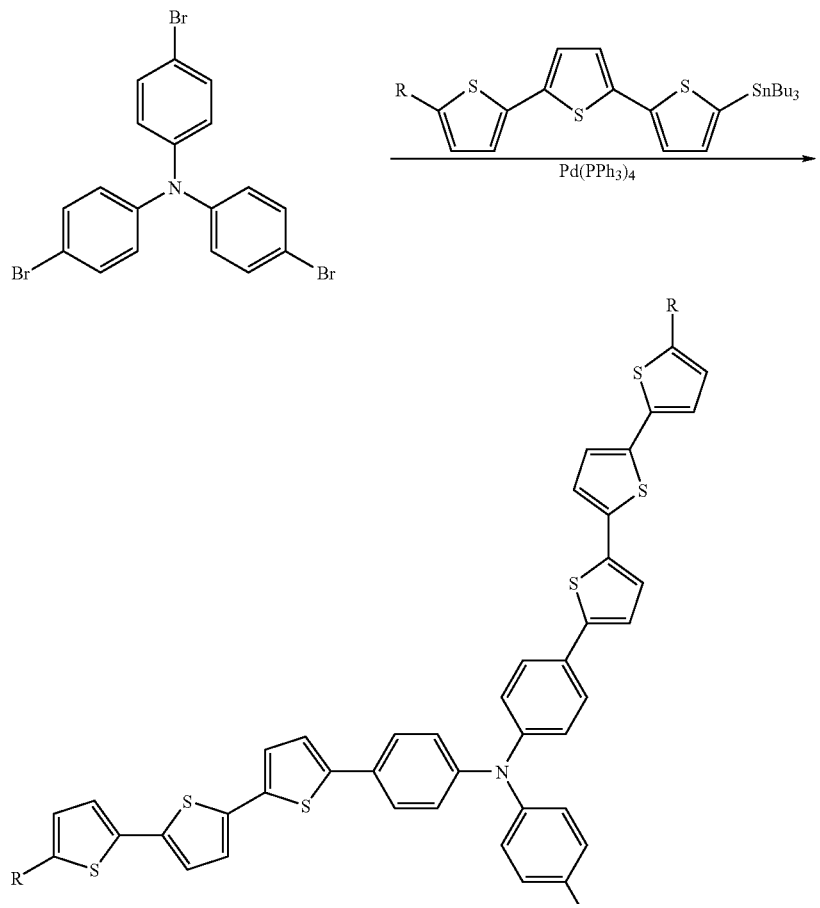

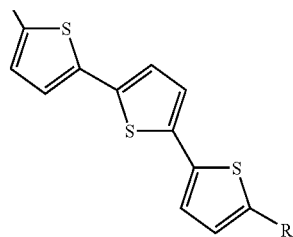
Reaction Scheme 3
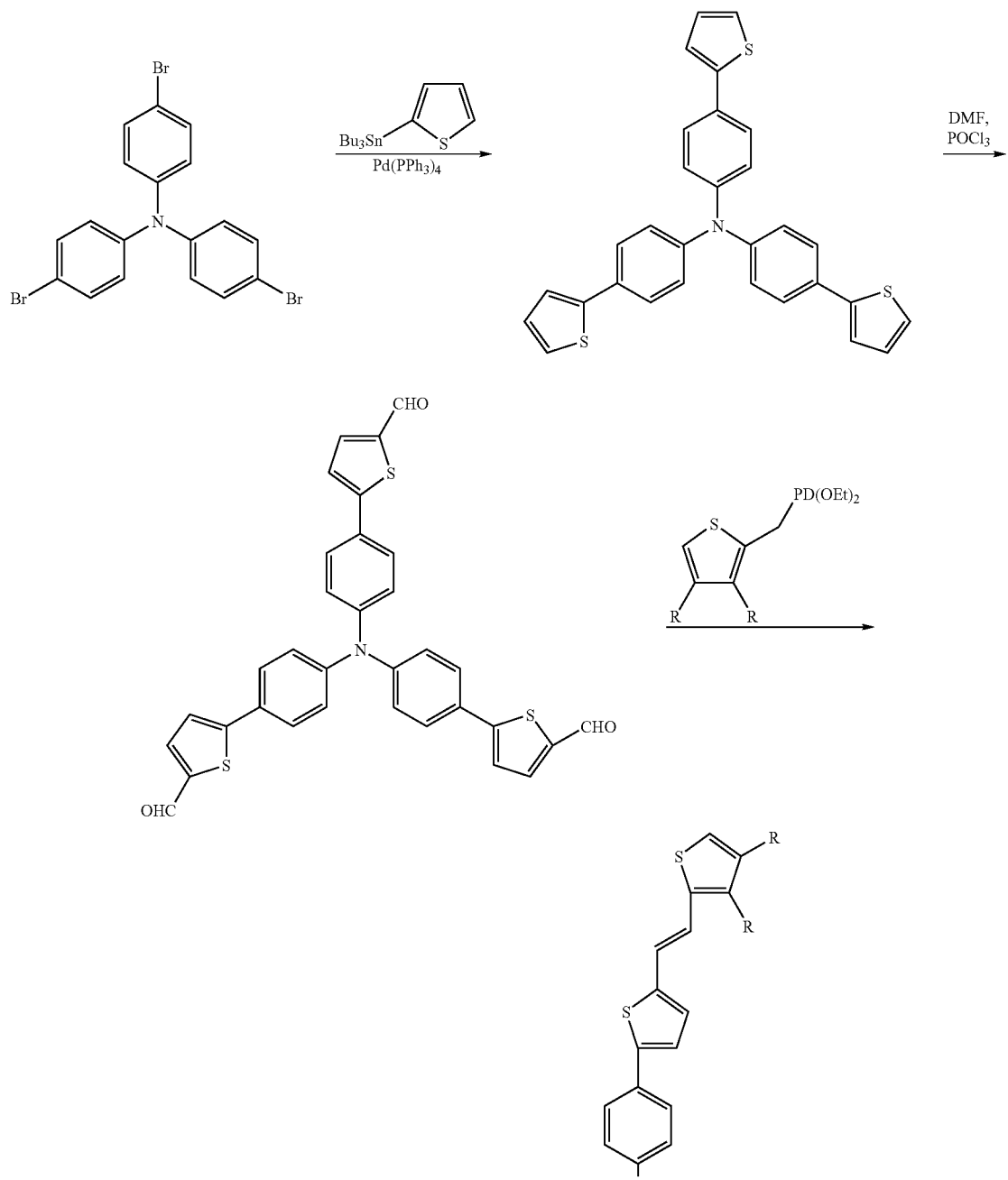

-continued

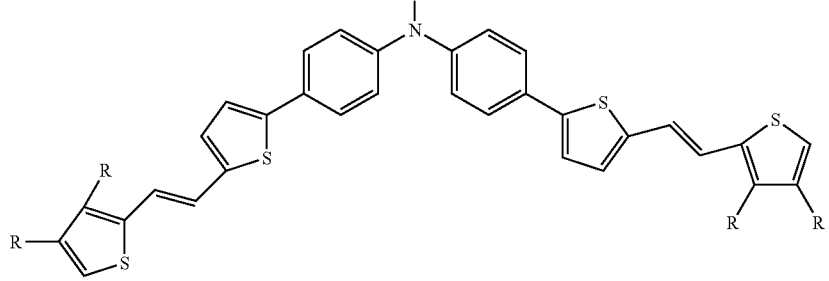

Reaction Scheme 4

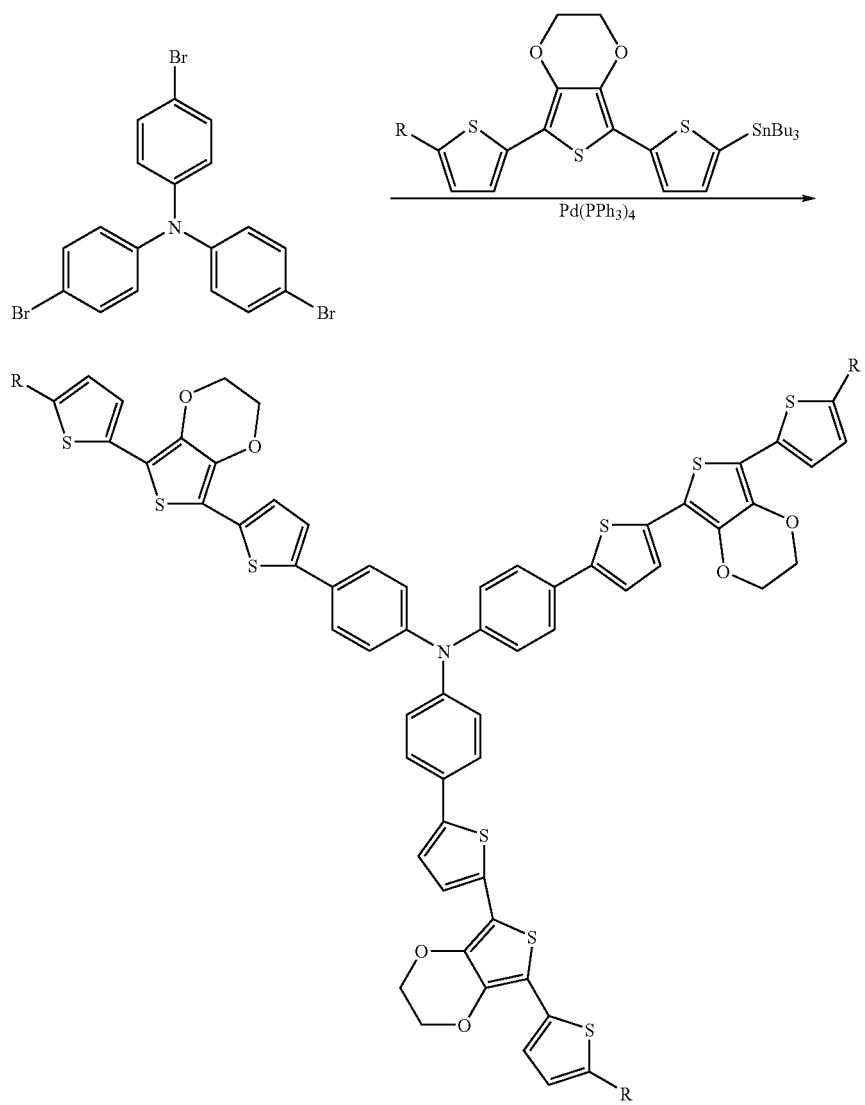

The substituents of the low molecular weight conjugated nitrogen compounds thus prepared can be controlled in order to facilitate a subsequent solution process. As a result, the low molecular weight conjugated nitrogen compounds can be coated at room temperature by already known coating techniques. Specifically, the conjugated nitrogen compounds can be formed into a thin film by screen printing, printing, spin coating, spin casting, dipping, and ink spraying.

Embodiments of the present disclosure also provide a device fabricated using the low molecular weight conjugated nitrogen compound as an organic semiconductor material, a hole conducting material, or a light-emitting material.

Specific examples of the device according to embodiments of the present disclosure include organic thin film transistors (OTFTs), organic field effect transistors (OFETs), organic solar photovoltaic cells, and organic light emitting devices.

The low molecular weight conjugated nitrogen compound of embodiments of the present disclosure can be used as a material for an organic semiconductor layer of an OTFT or OFET, a hole conducting layer of an organic solar photovoltaic cell, or a light-emitting layer or hole conducting layer of an OLED by processes known in the art.

Embodiments of the present disclosure will now be described in more detail with reference to the following examples. However, these examples are given for the purpose of illustration and are not to be construed as limiting the scope of the disclosure.

PREPARATIVE EXAMPLE 1

Preparation of Low Molecular Weight Conjugated Nitrogen Compound (1)

First, 1 g (2 mmol) of tris(4-bromophenyl)amine (Aldrich) was dissolved in 100 ml of toluene, and then 2.9 ml (4.5 eq.) of 2-tributylstannylthiophene and 27 mg (1.1%) of $Pd(PPh_3)_4$ were added thereto. The mixture was refluxed under a nitrogen atmosphere for 12 hours. The reaction mixture was allowed to cool to room temperature, washed with brine twice, and dried over $MgSO_4$. After the solvent was evaporated, the obtained residue was washed with petroleum ether (PE), and dried, affording 0.87 g (yield: 85%) of tris[4-(2-thienyl)phenyl]amine as a pale yellow solid.

$^1$H NMR ($CDCl_3$) δ (ppm): 7.50 (d, 2H) 7.20 (m, 2H) 7.10 (d, 2H) 7.08 (dd, 1H)

500 mg (1 mmol) of the tris[4-(2-thienyl)phenyl]amine was dissolved in 30 ml of 1,2-dichloroethane and DMF (0.37 g), and then 0.78 g (5 eq.) of $POCl_3$ was added thereto. The mixture was refluxed under a nitrogen atmosphere for 15 hours. To the reaction mixture were added 50 ml of methylene chloride and 100 ml of a saturated aqueous sodium acetate solution. The resulting mixture was stirred for 2 hours. The

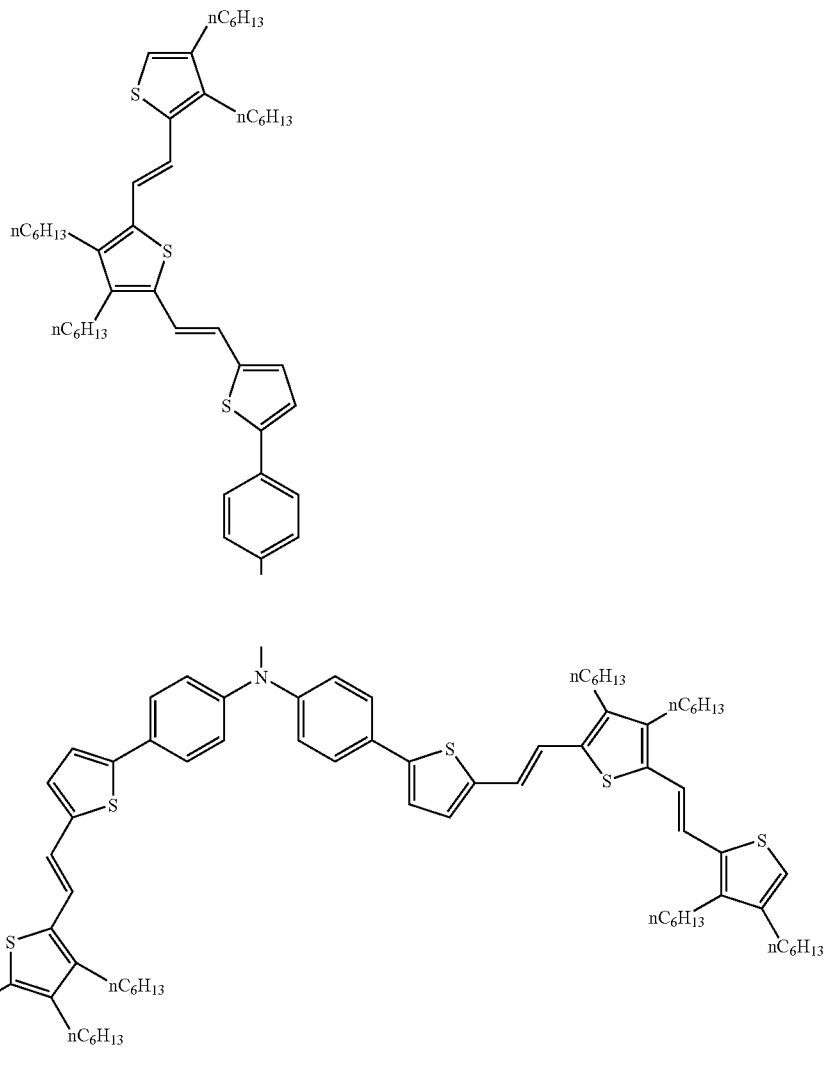

Compound 1 obtained organic phase was separated, washed with water, and dried over MgSO$_4$. The solvents were evaporated, and then the residue was purified by column chromatography, affording 0.53 g (yield: 90%) of tris[4-(5-formyl-2-thienyl)phenyl]amine as an orange solid.

$^1$H NMR (CDCl$_3$) δ (ppm): 9.90 (s, 1H, CHO) 7.70 (d, 1H) 7.60 (d, 1H) 7.30 (d, 2H) 7.20 (d, 2H)

140 mg (0.2 mmol) of the tris[4-(5-formyl-2-thienyl)phenyl]amine and 0.66 g (5 eq.) of diethyl {5-[(3,4-dihexyl-2-thienyl)-ethen-2-yl]-3,4-dihexyl-2-thienyl}}methylphosphonate were dissolved in 30 ml of anhydrous THF, and then potassium tertiobutyrate (120 mg) was added thereto under a nitrogen atmosphere. After the mixture was stirred for 1.5 hours, 120 ml of methylene chloride was added thereto. The obtained organic phase was washed with water, and dried over MgSO$_4$. The solvents were evaporated, and the residue was purified by column chromatography, affording 0.38 g (yield: 76%) of the final compound as a red oil.

$^1$H-NMR (CDCl$_3$) δ (ppm): 7.50 (d, 2H), 7.15 (d, 1H), 7.15 (d, 2H), 7.05 (d, 1H), 7.00 (d, 1H), 6.95 (m, 3H), 6.75 (s, 1H), 2.50 (m, 8H), 1.40 (m, 32H), 0.90 (m, 12H)

Figure 2:
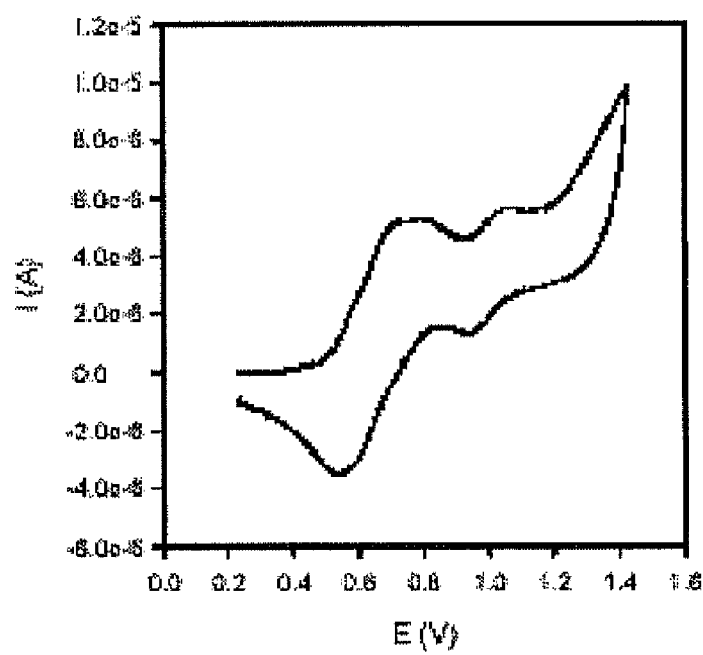
FIG. 2 is a cyclic voltammogram of a low molecular weight conjugated nitrogen compound synthesized in Preparative Example 1.

The UV-VIS absorbance and cyclic voltammogram (solvent: 0.10 M Bu$_4$NPF$_6$—CH$_2$Cl$_2$, scan rate: 100 mVs$^{-1}$) of the final compound were measured, and the results are shown in FIGS. 1 and 2, respectively. The graphs shown in FIGS. 1 and 2 demonstrate that the conjugated nitrogen compound absorbs UV-VIS light at a broad range of wavelengths and shows highly stable oxidation-reduction reactivity.

PREPARATIVE EXAMPLE 2

Preparation of Low Molecular Weight Conjugated Nitrogen Compound (2)

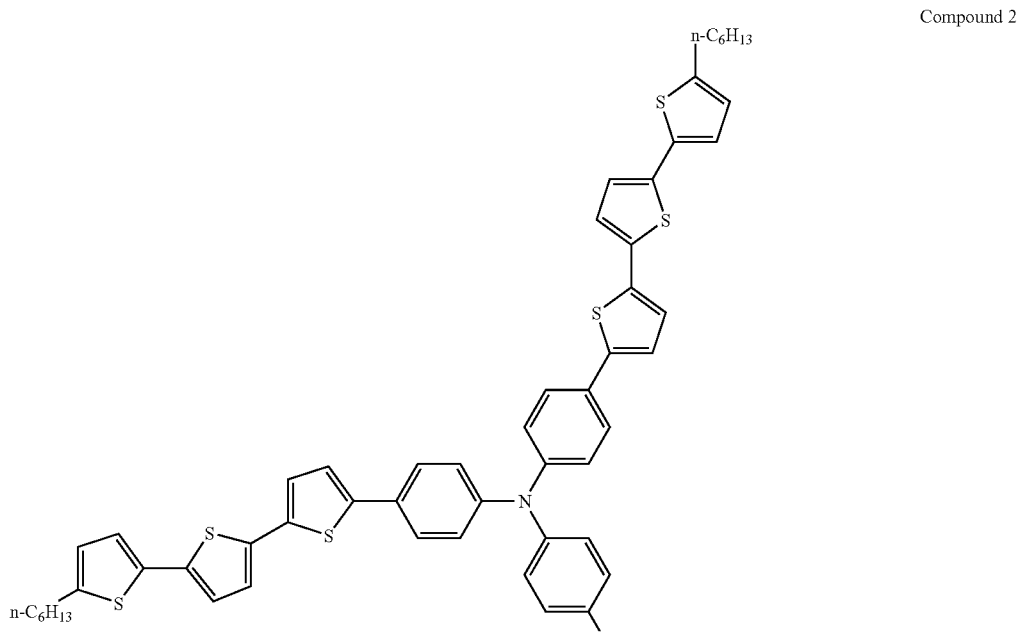

Compound 2

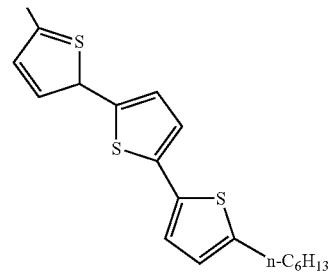

120 mg (0.25 mmol) of tris(4-bromophenyl)amine (Aldrich) was dissolved in 12 ml of toluene, and then 5″-hexyl-2-tributylstannyl-5,2′:5,2″-terthiophene (7.25 eq.) and 20 mg (5%) of Pd(PPh$_3$)$_4$ were added thereto. The mixture was refluxed under a nitrogen atmosphere for 16 hours. The reaction mixture was allowed to cool to room temperature. After the toluene was evaporated, the resulting residue was dissolved in methylene chloride. The obtained organic phase was washed with brine twice, and dried over MgSO$_4$. After the solvents were evaporated, the obtained residue was washed with petroleum ether (PE), and dried, affording 0.19 g (yield: 65%) of the final compound as an orange solid.

$^1$H-NMR (CDCl$_3$) δ (ppm) 7.48 (d, 2H), 7.14 (d, 2H), 7.13 (d, 1H), 7.08 (d, 1H), 7.03 (d, 1H), 6.96 (d, 1H), 6.94 (d, 1H), 6.66 (d, 1H), 2.81 (t, 2H), 1.69 (qt, 2H), 1.35 (m, 6H), 0.93 (t, 3H)

PREPARATIVE EXAMPLE 3

Preparation of Low Molecular Weight Conjugated Nitrogen Compound (3)

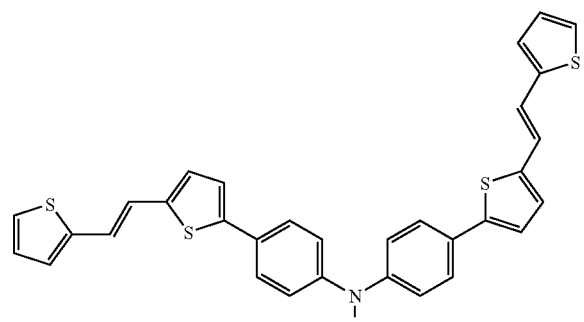

Compound 3

-continued

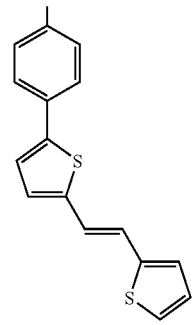

300 mg (yield: 70%) of the final compound as an orange solid was prepared in the same manner as in Preparative Example 1, except that tris[4-5-(formyl-2-thienyl)phenyl]amine 300 mg and thienyl-2-methyl-diethyl phosphonate 549 mg were used.

$^1$H-NMR (CDCl$_3$) δ (ppm) 7.50 (d, 2H), 7.10 (d, 1H), 7.00 (d, 2H), 6.95 (d, 1H), 6.90 (d, 1H), 6.73 (d, 1H), 6.70 (d, 1H), 6.65 (m, 2H)

PREPARATIVE EXAMPLE 4

Preparation of Low Molecular Weight Conjugated Nitrogen Compound (4)

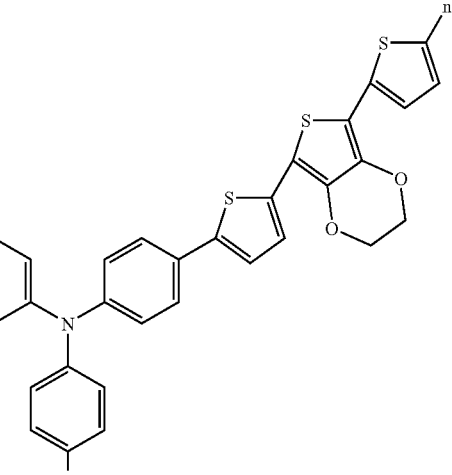

Compound 4

-continued

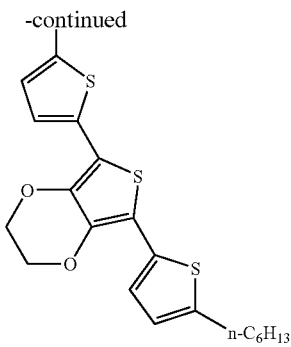

320 mg (0.67 mmol) of tris(4-bromophenyl)amine (Aldrich), 3.17 g (7 eq.) of 3',4'-ethylenedioxy-5"-hexyl-2-tributylstannyl-5,2':5,2"-terthiophene and 40 mg (5%) of Pd(PPh$_3$)$_4$ were dissolved in 30 ml of toluene. The mixture was refluxed under a nitrogen atmosphere for 15 hours. The reaction mixture was allowed to cool to room temperature. After the toluene was evaporated, the resulting residue was dissolved in methylene chloride. The obtained organic phase was washed with water, and dried over MgSO$_4$. After the solvents were evaporated, the obtained residue was washed with petroleum ether (PE) and dissolved in methylene chloride. PE was added to the solution to obtain a precipitate. The precipitate was filtered to afford 0.42 g (yield: 45%) of the final compound as a brown solid.

$^1$H-NMR (CDCl$_3$) δ (ppm): 7.50 (d, 2H), 7.16 (d, 2H), 7.12 (d, 2H), 7.03 (d, 1H), 6.69 (d, 1H), 4.39 (d, 4H), 2.80 (t, 2H), 1.68 (qt, 2H), 1.38 (m, 2H), 1.32 (m, 4H), 0.89 (t, 3H)

EXAMPLE 1

Fabrication of Device and Measurement of Photovoltaic Efficiency

Figure 3:
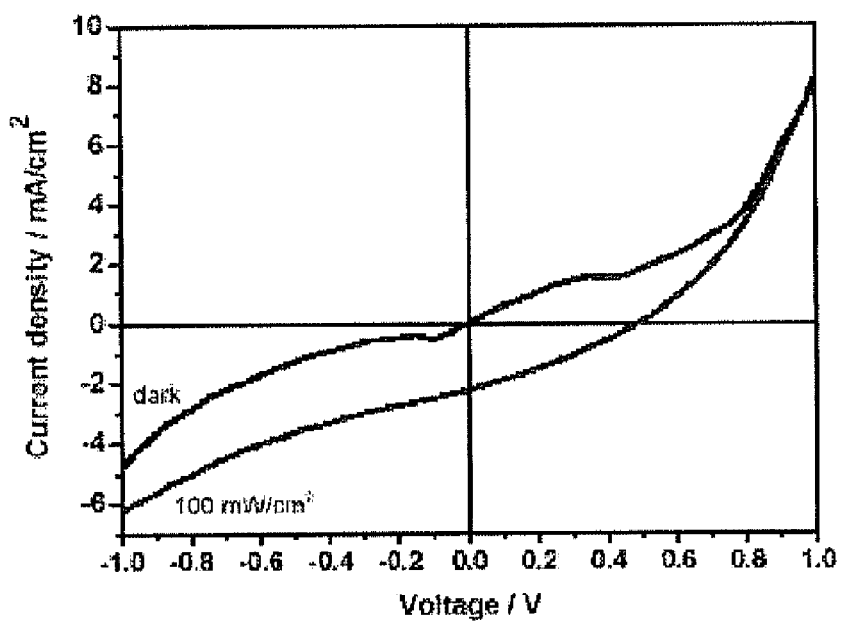
FIG. 3 is a graph showing the current-voltage (I-V) characteristics of a device fabricated in Example 1.

An 80 nm-thick layer of a conductive polymer (Baytron P, Bayer) was formed on a glass substrate on which an ITO electrode was formed. Thereafter, the low molecular weight conjugated nitrogen compound synthesized in Preparative Example 1 was spin-cast on the conductive polymer layer to form a 100 nm-thick organic semiconductor layer. Then, a 60 nm-thick counter electrode made of aluminum was formed on the organic semiconductor layer to fabricate a device for the measurement of photovoltaic efficiency. The current-voltage characteristics were measured under AM 1.5 illumination conditions, and the results are plotted in FIG. 3. The photovoltaic efficiency of the device was measured to be 0.35% at a light intensity of 100 mW/cm$^2$, as calculated from the I-V curves shown in FIG. 3.

EXAMPLE 2

Fabrication of Device and Measurement of Electroluminescence Spectrum

Figure 4:
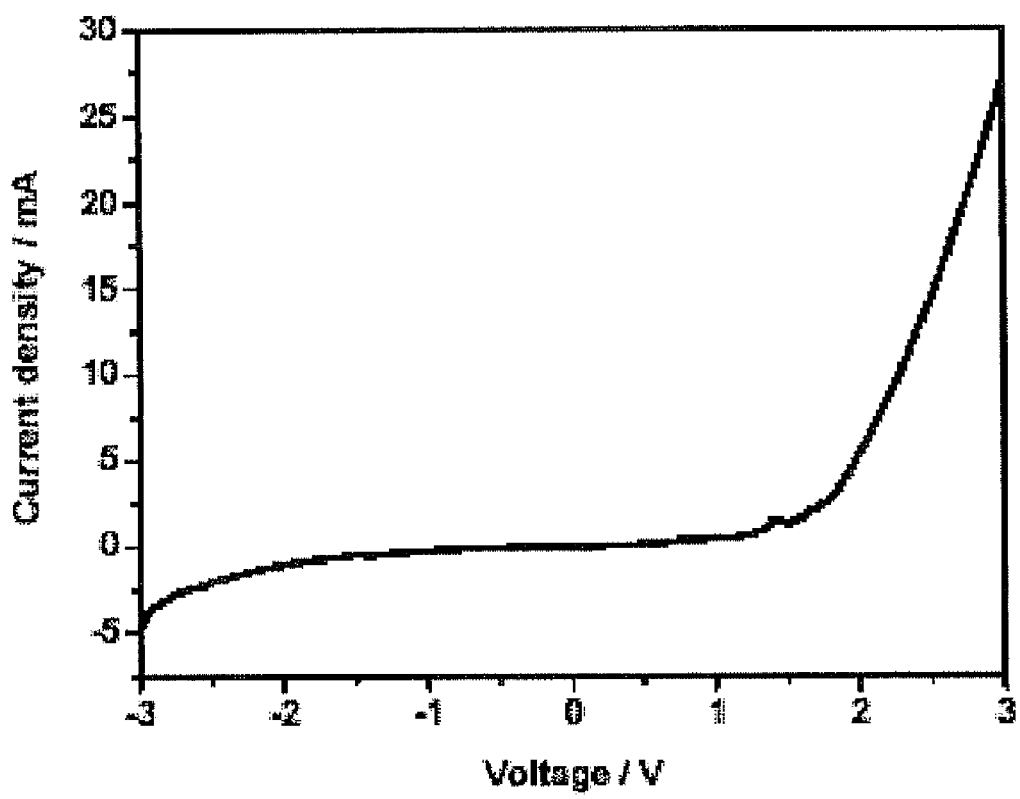
FIG. 4 is a graph showing the current-voltage (I-V) characteristics of a device fabricated in Example 2.
Figure 5:
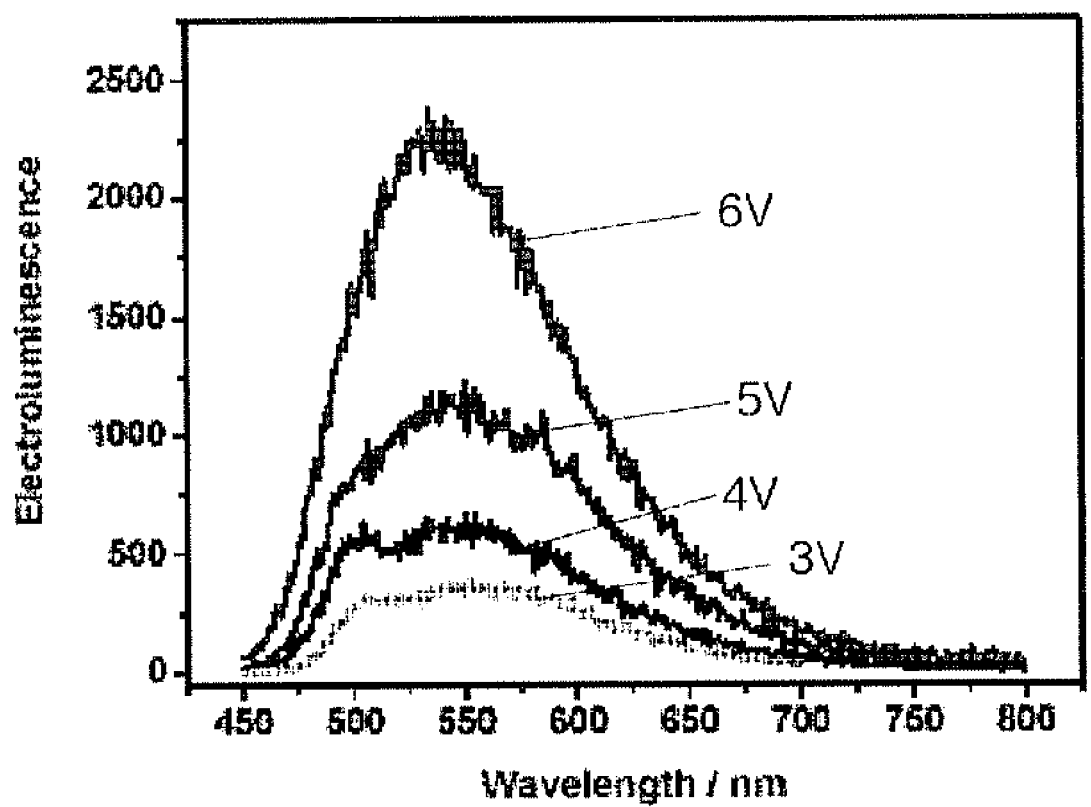
FIG. 5 is an electroluminescence spectrum of a device fabricated in Example 2.

A device was fabricated in the same manner as in Example 1, except that the low molecular weight conjugated nitrogen compound prepared in Preparative Example 4 was used. The current-voltage characteristics of the device were measured under the same conditions as in Example 1, and the results are shown in FIG. 4. In addition, the electroluminescence spectrum of the device was measured, and the results are shown in FIG. 5. The graphs shown in FIGS. 4 and 5 indicate that the conjugated nitrogen compound shows luminescence properties and has a low threshold voltage.

As apparent from the above description, the low molecular weight conjugated nitrogen compound of embodiments of the present disclosure may be a low molecular weight organic semiconductor compound having a novel structure. In addition, the conjugated nitrogen compound of embodiments of the present disclosure can be spin-coated at room temperature, may be stable, and may be superior in electrical conductivity and luminescence efficiency. Therefore, the conjugated nitrogen compound of embodiments of the present disclosure can be widely applied to the fabrication of organic thin film transistors (OTFTs), organic field effect transistors (OFETs), organic solar photovoltaic cells, and organic light emitting devices.

Although the preferred embodiments of embodiments of the present disclosure have been disclosed for illustrative purposes, those skilled in the art will appreciate that various modifications, additions and substitutions are possible, without departing from the scope and spirit of the disclosure as disclosed in the accompanying claims.

What is claimed is:

1. A low molecular weight conjugated nitrogen compound represented by Formula 1 below:

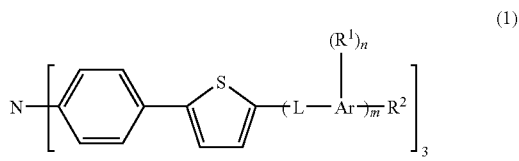

wherein L is a single bond;
Ar is thiophene, benzo[c]thiophene, or 3,4-ethylenedioxythiophene;
R$^1$ is selected from the group consisting of hydrogen, C$_{1-10}$ linear and branched alkyl groups, C$_{1-10}$ linear and branched alkoxy groups, C$_{1-10}$ linear and branched hydroxyalkyl groups, and C$_{1-10}$ linear and branched alkoxyalkyl groups;
R$^2$ is selected from the group consisting of C$_{1-10}$ linear and branched alkyl groups, C$_{1-10}$ linear and branched alkoxy groups, C$_{1-10}$ linear and branched hydroxyalkyl groups, C$_{1-10}$ linear and branched alkoxyalkyl groups, and substituted thienyl groups;
m is an integer between 1 and 5; and
n is an integer between 1 and 3.

2. The conjugated nitrogen compound according to claim 1, wherein the conjugated nitrogen compound is selected from the group consisting of compounds represented by Formulae 4 or 6 below:

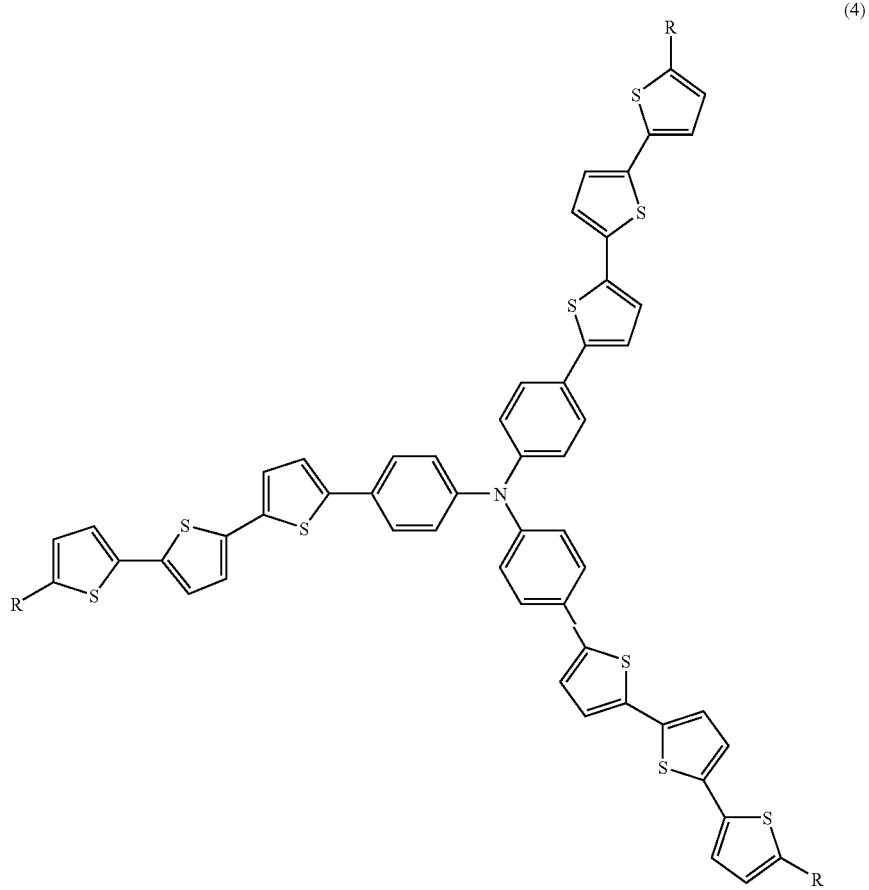

(4)

wherein R is selected from the group consisting of $C_{1-10}$ linear and branched alkyl groups, $C_{1-10}$ linear and branched alkoxy groups, $C_{1-10}$ linear and branched hydroxyalkyl groups, and $C_{1-10}$ linear and branched alkoxyalkyl groups, and

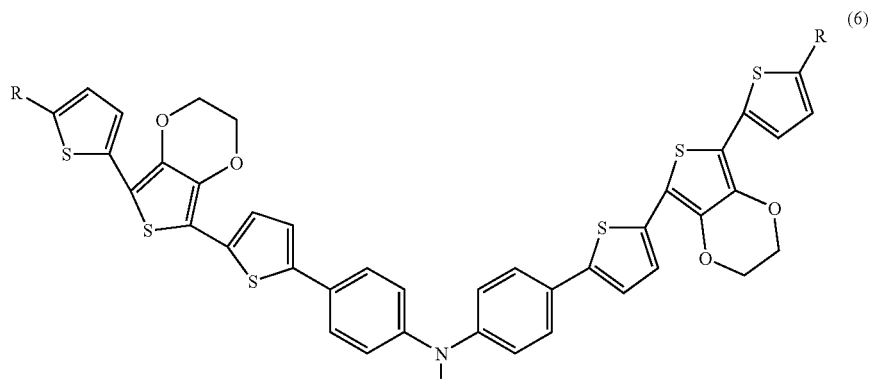

(6)

-continued

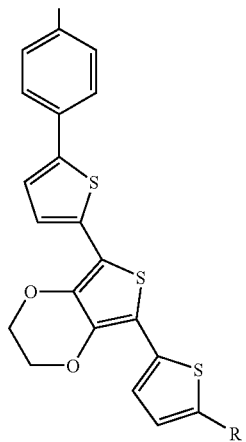

wherein R is selected from the group consisting of hydrogen, $C_{1-10}$ linear and branched alkyl groups, $C_{1-10}$ linear and branched alkoxy groups, $C_{1-10}$ linear and branched hydroxyalkyl groups, and $C_{1-10}$ linear and branched alkoxyalkyl groups.

3. An organic thin film transistor comprising the conjugated nitrogen compound according to claim 1 as a material for a channel layer.

4. The organic thin film transistor according to claim 3, wherein the material for a channel layer is formed into a thin film by screen printing, printing, spin coating, spin casting, dipping, or ink spraying.

5. A solar photovoltaic cell comprising the conjugated nitrogen compound according to claim 1 as a hole conducting material.

6. The solar photovoltaic cell according to claim 5, wherein the hole conducting material is formed into a thin film by screen printing, printing, spin coating, spin casting, dipping, or ink spraying.

7. An organic light-emitting device comprising the conjugated nitrogen compound according to claim 1 as a light-emitting material or a hole conducting material.

8. The organic light-emitting device according to claim 7, wherein the light-emitting material or hole conducting material is formed into a thin film by screen printing, printing, spin coating, spin casting, dipping, or ink spraying.

9. A conjugated nitrogen compound represented by Formula 1 below:

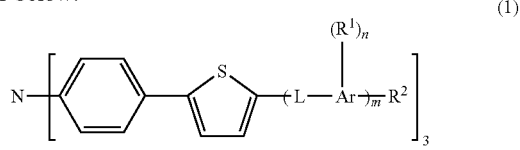

(1)

wherein L is a single bond;
Ar is thiophene, benzo[c]thiophene, or 3,4-ethylenedioxythiophene;
$R^1$ is selected from the group consisting of hydrogen, $C_{1-10}$ linear and branched alkyl groups, $C_{1-10}$ linear and branched alkoxy groups, $C_{1-10}$ linear and branched hydroxyalkyl groups, and $C_{1-10}$ linear and branched alkoxyalkyl groups;
$R^2$ is a substituted thienyl group;
m is an integer between 1 and 5; and
n is an integer between 1 and 3.

10. The conjugated nitrogen compound according to claim 9, wherein $R^1$ is hydrogen.

11. The conjugated nitrogen compound according to claim 9, wherein $R^2$ is substituted with hydrogen, a $C_{1-10}$ linear or branched alkyl group, a $C_{1-10}$ linear or branched alkoxy group, a $C_{1-10}$ linear or branched hydroxyalkyl group or a $C_{1-10}$ linear or branched alkoxyalkyl group.

12. The conjugated nitrogen compound according to claim 1, wherein $R^2$ is substituted with a $C_{1-10}$ linear alkyl group.

* * * * *